US008884087B2

(12) United States Patent
Koh et al.

(10) Patent No.: US 8,884,087 B2
(45) Date of Patent: Nov. 11, 2014

(54) BLOCK COORDINATION COPOLYMERS (75) Inventors: Kyoung Moo Koh, Ann Arbor, MI (US); Antek G. Wong-Foy, Ann Arbor, MI (US); Adam J. Matzger, Ann Arbor, MI (US); Annabelle I. Benin, Des Plaines, IL (US); Richard R. Willis, Des Plaines, IL (US)

(73) Assignees: UOP LLC, Des Plaines, IL (US); The Regents of the University of Michigan, Ann Arbor, MI (US)

( * ) Notice: Subject to any disclaimer, the term of this patent is extended or adjusted under 35 U.S.C. 154(b) by 361 days.

(21) Appl. No.: 12/478,034

(22) Filed: Jun. 4, 2009

(65) Prior Publication Data
US 2010/0222619 A1    Sep. 2, 2010

Related U.S. Application Data (60) Provisional application No. 61/156,043, filed on Feb. 27, 2009.

(51) Int. Cl.
| | |
|---|---|
| *B01J 31/06* | (2006.01) |
| *C07C 5/52* | (2006.01) |
| *C07C 4/08* | (2006.01) |
| *C07C 5/00* | (2006.01) |
| *C07F 1/08* | (2006.01) |
| *C07C 2/66* | (2006.01) |
| *C07C 5/42* | (2006.01) |
| *C07C 5/02* | (2006.01) |
| *C07C 4/06* | (2006.01) |
| *C07C 1/04* | (2006.01) |
| *C07F 3/06* | (2006.01) |
| *C07C 5/22* | (2006.01) |
| *C07C 5/32* | (2006.01) |
| *C07C 2/58* | (2006.01) |

(52) U.S. Cl.
CPC ... *C07C 4/06* (2013.01); *C07F 1/08* (2013.01); *C07C 2/66* (2013.01); *C07C 5/42* (2013.01); *C07C 5/02* (2013.01); *C07C 1/0445* (2013.01); *C07F 3/06* (2013.01); *C07C 5/22* (2013.01); *C07C 5/32* (2013.01); *C07C 2/58* (2013.01)
USPC ............ 585/250; 502/159; 585/470; 585/752

(58) Field of Classification Search
None
See application file for complete search history.

(56) References Cited

U.S. PATENT DOCUMENTS

| | | | |
|---|---|---|---|
| 4,405,771 | A | 9/1983 | Jagur |
| 4,814,316 | A | 3/1989 | Pellet et al. |
| 5,648,508 | A | 7/1997 | Yaghi |
| 6,930,193 | B2 | 8/2005 | Yaghi et al. |

(Continued)

FOREIGN PATENT DOCUMENTS

WO    WO2009/029848 A1    3/2009

OTHER PUBLICATIONS

Chen et al. Inorganic Chemistry, vol. 42 (4), 944, 2003.*
Koh et al. Angew. Chem. Int. Ed., 2008, 47, 677-680.*

(Continued)

*Primary Examiner* — Yun Qian
(74) *Attorney, Agent, or Firm* — Maryann Maas (57) ABSTRACT

The present invention provides compositions of crystalline coordination copolymers wherein multiple organic molecules are assembled to produce porous framework materials with layered or core-shell structures. These materials are synthesized by sequential growth techniques such as the seed growth technique. In addition, the invention provides a simple procedure for controlling functionality.

15 Claims, 5 Drawing Sheets

(56) References Cited

U.S. PATENT DOCUMENTS

| | | |
|---|---|---|
| 7,109,297 B2 | 9/2006 | Lo et al. |
| 7,309,380 B2 | 12/2007 | Muller et al. |
| 7,343,747 B2 | 3/2008 | Muller et al. |
| 8,324,323 B2 * | 12/2012 | Koh et al. .................. 525/389 |
| 2006/0230926 A1 | 10/2006 | Fritsch et al. |
| 2008/0261101 A1 | 10/2008 | Gomes et al. |
| 2009/0018334 A1 | 1/2009 | Bae et al. |
| 2009/0062409 A1 | 3/2009 | Matzger et al. |
| 2011/0021341 A1 * | 1/2011 | Matzger et al. .................. 502/22 |

OTHER PUBLICATIONS

Kitagawa, S. et al., "Functional Porous Coordination Polymers", Angew. Chem. Int. Ed. 43 (2004) 2334-2375.

Koh, K. et al., "A Crystalline Mesoporous Coordination Copolymer with High Microporosity", Angew. Chem. Int. Ed., 2008, 47, 677-680.

Li, Hallian et al., "Design and synthesis of an exceptionally stable and highly porous metal-organic framework", Nature, 1999, 402, 276-279.

Eddaoudi, M. et al., "Systematic Design of Pore Size and Functionality in Isoreticular MOFs and Their Application in Methane Storage", Science, 2002, 295, 269-472.

Chun, H. et al., "Synthesis, X-ray Crystal Structures and Gas Sorption Properties and Gas sorption Properties . . . ", Chem. Eur. J., 2005, 11, 3521-3529.

Burrows, D. et al., "Post-Synthetic Modification of Tagged Metal-Organic Frameworks", Angew. Chem. Int. Ed., 2008, 47, 8482-8486.

MacDonald, J.C. et al., "Design of Layered Crystalline Materials Using Coordination Chemistry and Hydrogen Bonds", J. Am. Chem. Soc., 2000, 122, 11692-11702.

Luo, T.J. et al., "Fabrication of Complex Crystals Using Kinetic Control, Chemical Additives and Epitaxial Growth", Chem. Mater. 2004, 16, 4916-4927.

Ferlay, S. et al., "Crystalline Molecular Alloys", Chem. Comm. 2004, 7, 788-789.

DeChambenoit, P. et al., "From Tectons to Composite Crystals", Cryst. Growth Des., 2005, 5, 2310-2312.

Bres, E. et al., "Investigations on crystalline interface within a molecular composite crystal by microscopic techniques", J. Mater. Chem., 2007, 17, 1559-1562.

Noveron, J.C. et al., "Engineering the Structure and Magnetic Properties of Crystalline Solids . . . ", J. Am. Chem. Soc., 2002, 124, 6613-6625.

Dugan, E. et al., "Covalent modification of a metal-organic framework with isocyanates . . . ", Chem. Commun., 2008, 29, 3366-3368.

Tanabe, K.K. et al., "Systematic Functionalization of a Metal-Organic Framewrk via a Postsynthetic Modification Approach", J. Am. Chem. Soc 2008, 8508-8517.

Furukawa, "Heterogenously Hybridized Porous Coordination Polymer Crystals: Fabrication of Heterometallic Core-Shell Single Crystals with an In-Plane Rotational Epitaxial Relationship", Angew. Chem. Int. Ed, 2009, vol. 48, pp. 1766-1770.

U.S. Office Action, U.S. Appl. No. 12/478,018, Notification date: Sep. 16, 2011 and response to U.S. Office Action by applicant date: Dec. 14, 2011, Koh et al.

U.S. Office Action, U.S. Appl. No. 12/478,042, Notification date: Sep. 9, 2011 and response to U.S. Office Action by applicant date: Dec. 14, 2011, Koh et al.

U.S. Office Action, U.S. Appl. No. 12/478,018, Notification date: Jan. 24, 2012, Koh et al.

U.S. Office Action, U.S. Appl. No. 12/478,042, Notification date: Jan. 25, 2012, Koh et al.

* cited by examiner

BLOCK COORDINATION COPOLYMERS

CROSS-REFERENCE TO RELATED APPLICATION

This application claims priority from Provisional Application Ser. No. 61/156,043 filed Feb. 27, 2009, the contents of which are hereby incorporated by reference in its entirety.

STATEMENT REGARDING FEDERALLY SPONSORED RESEARCH OR DEVELOPMENT

This invention was made under the support of the United States Government, United States Department of Energy though the National Energy technology Laboratory under Award No. DE-FC26-07NT42121. The United States Government has certain rights in the invention.

BACKGROUND OF THE INVENTION

Known substance classes of porous solids are called metal organic frameworks (MOF) or coordination polymers. The theory of coordination bonds developed by Alfred Werner [A. Werner, Z. Anorg. Allg. Chem. 3 (1893) 267] made it possible for the first time to understand the experimental results of complex inorganic chemistry. Stable coordination polymers are obtained by adding organic molecules capable of complex formation, like diamines or diacids, to dissolved inorganic salts. The distances between the metal ions as coordination centers can be set in a wide range through the structure, in particular of the organic components, and result in micro- to mesoporous substances. Coordination polymers can thus be varied and are substantially documented [S. Kitagawa, et al. Angew. Chem. Int. Ed. 43 (2004) 2334].

The ability to synthesize coordination polymers with porosity results in a new class of materials that are crystalline molecular sieves. The atomic structure of any coordination polymers can be determined by x-ray crystallography, the dimensions of the pores or channels can be determined with excellent certainty. The internal surface areas of some porous coordination polymers are significantly greater than other porous materials. The pore sizes/shapes are highly tunable and large pore sizes can be synthesized when compared to know zeolites. Functionalization of the backbones or frameworks in these materials can be achieved by starting the synthesis with organic linkers with functional groups already installed or by post synthesis modification.

Recently, the coordination copolymerization method with two topologically distinct linkers was reported, and can give rise to a microporous coordination polymer (MCP) with a previously unattainable mesoporous structure [K. Koh, A. G. Wong-Foy and A. J. Matzger, Angew. Chem., Int. Ed., 47, (2008), 677]. The first example of this strategy, UMCM-1 (University of Michigan Crystalline Materials), illustrated that instead of a mixture of crystalline phases arising from the independent assembly of a single linker type, a novel phase incorporating all organic components can be produced by controlling the mole ratio of each organic linker.

SUMMARY OF THE INVENTION

The present invention describes a new class of materials, coordination copolymers. Production of these materials involves sequential growth techniques such as the seed growth method, and the three dimensional propagation of the second or higher shells generates the layer features. The materials may be used in processes such as separation processes and as catalysts for reactions.

The new material is a coordination copolymer comprising at least a first coordination polymer and a second coordination polymer wherein the first and second coordination polymers are not identical. The first coordination polymer and the second coordination polymer may be present in a first and second layered configuration. Optionally, at least a third coordination polymer may be layered on the second layer. The third coordination polymer may be the same as the first layer. The third coordination polymer may have a different composition or a different structure from that of either the first or the second coordination polymer. The first and second layered configuration may form a core and shell configuration. At least a third coordination polymer may be layered on the shell. The third coordination polymer may be the same as the core. The third coordination polymer may have a different composition or a different structure from that of either the first or the second coordination polymer.

One method of making a coordination copolymer involves adding at least one source of metal cations and at least one organic linking compound to a solvent to form a first solution or colloidal suspension; treating the first solution or colloidal suspension to form crystals of a first coordination polymer; adding at least one source of metal cations and at least one organic linking compound to a solvent to form a second solution or colloidal suspension wherein the second solution is not identical to the first solution or colloidal suspension; adding crystals of the first coordination polymer to the second solution or colloidal suspension; and treating the second solution or colloidal suspension to form crystals of a second coordination polymer as a layer over one or more crystals of the first coordination polymer forming a coordination copolymer wherein the first coordination polymer is not identical to the second coordination polymer. The crystals of the first coordination polymer may be of a size ranging from about 10 nanometers to about 1 micron. The coordination copolymers may be made by a "one-pot" method as well. For example, a coordination copolymer may be made by adding at least one source of metal cations and at least one organic linking compound in a solvent to form a solution or colloidal suspension; treating the solution or colloidal suspension to form crystals of a first coordination polymer; adding at least one additional reagent selected from the group consisting of a second source of metal cations, a second organic linking compound, and a combination thereof, to the solution or colloidal suspension; and treating the solution to form crystals of a second coordination polymer as layer over one or more crystals of the first coordination polymer forming a coordination copolymer wherein the first coordination polymer is not identical to the second coordination polymer.

The coordination copolymer may be used in a process for separating a first component from a second component of a mixture by contacting the mixture with a coordination copolymer comprising at least a first coordination polymer and a second coordination polymer wherein the first and second coordination polymers are not identical. The coordination copolymer may also be used as a catalyst in a chemical reaction. For example, the coordination copolymer may be used for converting at least one reactant by contacting a feed comprising at least one reactant with a coordination copolymer comprising at least a first coordination polymer and a second coordination polymer wherein the first and second coordination polymers are not identical and wherein at least one coordination polymer comprises a catalytic function, to give a converted product.

DETAILED DESCRIPTION OF THE INVENTION

The present invention provides a novel class of materials called block coordination copolymers, which comprise at least two different coordination polymers. The two different coordination polymers are spatially contiguous and the coordination copolymer exhibits regions or blocks of the first coordination polymer and of the second coordination polymer. The at least two different coordination polymers may be porous coordination polymers or non-porous coordination polymers or a combination thereof.

Processes described herein demonstrate the formation of block coordination copolymers which comprise at least two non-identical coordination polymers. For example, two coordination polymers may each have different pore sizes, and when used to form a single coordination copolymer the resulting multi-compositional coordination copolymer may have at least one portion having a first pore size and at least one other portion having a second pore size. More than two coordination polymers may be used to form the multicompositional coordination copolymer resulting in multiple portions of the composite having differing pore sizes. Thus, a novel class of materials with new properties can be produced. One benefit of the process is that the coordination polymers used to make the composite and hence the pore sizes can be selected depending upon the application within which the composite will be used. Furthermore, depending upon the process of making the composite, control may be exercised during the formation of the composite to locate a particular pore size in a specific region of the composite. Therefore, if desired, coordination copolymers may be formed for specific applications by selecting the starting coordination polymers and the process for making the coordination copolymer. It is envisioned that a coordination copolymer may be synthesized to have a high selectivity as well as a high capacity in applications such as size selective separations and size and or shape selective catalysis.

Examples of suitable coordination polymers for use in synthesizing the composite coordination copolymer will be first described herein, and then the process for forming the composite coordination copolymer will be described.

The coordination polymers used to form a coordination copolymer composite define a molecular framework. The coordination polymers contain a plurality of metal atoms or metal clusters linked together by a plurality of organic linking ligands. The linking ligand coordinates two or more metal atoms or metal clusters. The organic linking ligands may be the same or different. The organic linking ligands may be charge neutral, or each organic linking ligand is derived from a negatively charged multidentate ligand. Characteristically the linking ligands of a coordination copolymer include a first linking ligand having a first backbone, and a second linking ligand having a second backbone. In the most common case, the first and second backbones are identical, having, for example, the same aromatic ring or straight chain hydrocarbon structures. However, it is also understood that the first and second backbones may be different. For example, the first and second backbones may have different ring or straight chain structures; the first and second backbones may have the same ring or straight chain structures but be substituted with different functional groups; or the first and second backbones may be hydrocarbons, or may have one or more atoms replaced by a heteroatom such as N, O, or S. The coordination copolymers may be in crystal form such as in crystal clusters, they may be catalytically active, and the surface of the coordination polymer may be polar or non-polar.

In one embodiment of the invention, each metal cluster of the coordination copolymer includes one or more metal ions with the organic linking ligands partially or fully compensating for the charges of the metal ions. In a specific embodiment, each metal cluster includes a metal ion or metalloid having a metal selected from the group consisting of Group 1 though 16 of the IUPAC Periodic Table of the Elements including actinides, lanthanides, and combinations thereof. Specific examples of useful metal ions include, but are not limited to, the metal ion selected from the group consisting of $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{+3}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{+}$, $Rh^{2+}$, $Rh^{3+}$, $Ir^{+}$, $Ir^{3+}$, $Ni^{2}$, $Ni^{+}$, $Pd^{2+}$, $Pd^{4+}$, $Pt^{2+}$, $Pt^{4+}$, $Cu^{2+}$, $Cu^{+}$, $Ag^{+}$, $Au^{+}$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sb^{2+}$, $Pb^{4+}$, $Pb^{2+}$, $As^{5+}$, $As^{3+}$, $As^{+}$, $Sb^{5+}$, $Sb^{3+}$, $Sb^{+}$, $Bi^{5+}$, $Bi^{3+}$ and $Bi^{+}$.

The coordination copolymers comprise coordination polymers that have organic linking ligands. In one embodiment of the invention, the organic linking ligand may be described by Formula I:

$$X_n Y \qquad (I)$$

wherein X is a functional group;
n is an integer that is equal to or greater than 2, and
Y is a hydrocarbon group or a hydrocarbon group having one or more carbon atoms replaced by a heteroatom.

In one embodiment, X is  $CE_2^-$, $C(Ar)_2^-$, $RC(=G)C=C(G')R$, or $R^1C(ZR^2)C=C(ZR^2)R^1$; E is O, S, Se, or Te; Z is N, P, or As; R $R^1$ $R^2$ are H, alkyl group, or aryl group; A is N, P, or As and G is O, S, Se, or Te. Suitable examples for X include, but are not limited to, $CO_2^-$, $CS_2^-$, $ROPO_2^-$, $PO_3^{-2}$, $ROPO_3^{-2}$, $PO_4^{-2}$, $ROAsO_2^-$, $AsO_3^{-2}$, $ROAsO_3^{-2}$, $SO_3^-$, $SO_4^-$, $SeO_3^-$, $SeO_4^-$, $TeO_3^-$ or $TeO_4^-$. In another embodiment, Y comprises a moiety selected from the group consisting of monocyclic aromatic ring, a polycyclic aromatic ring, a monocyclic heteroaromatic ring, a polycyclic heteroaromatic ring, alkyl groups having from 1 to 10 carbon atoms, and combinations thereof. In another embodiment, Y is alkyl, alkyl amine, aryl amine, alkyl aryl amine, or phenyl. In yet another embodiment, Y is a $C_{1-10}$ alkyl, a $C_{6-50}$ aromatic ring, or a $C_{4-24}$ heteroaromatic ring system. The organic linking ligands may be the same throughout a coordination polymer, or more than one organic linking ligand may be incorporated in a coordination polymer.

In one embodiment of the invention, the coordination copolymers are characterized by having an average pore dimension from about 2 to about 40 angstroms, from about 5 to about 30 angstroms, or from about 8 to about 20 angstroms as determined by nitrogen adsorption. In another embodiment of the invention the coordination copolymers are characterized by having a surface area greater than about 2000 $m^2/g$ as determined by the Langmuir method. In another embodiment, the coordination copolymers are characterized by having a surface area of greater than about 1000 to about 40000 m$^2$/g as determined by the Langmuir method. In yet another embodiment, the coordination polymer has a pore volume per grams of coordination polymer greater than about 0.1 cm$^3$/g as determined by nitrogen adsorption.

Furthermore, bulk properties of the multicompositional coordination copolymer may be controlled by varying the concentration of the different linkers in solution during syntheses of at least one of the coordination polymers, see Example 2. Controlling the bulk properties of coordination copolymers allow for the coordination copolymers to be synthesized for specific purposes which require specific bulk properties. For example, controlling the surface area of the coordination copolymer composite could allow an end user to use less material to accomplish a given task because of the higher surface area provides a significantly larger number of active sites.

Controlling the order of the addition of the linkers constitutes an approach to making the coordination copolymer and can be considered a seeded growth technique involving epitaxial growth of metal organic coordinated molecules with different components. The resultant composition of matter is a layered material derived from the nesting of the frameworks. Previously, techniques have relied on substitution of metal ions resulting in color contrast or magnetism changes. The technique herein allows for engineering of multi layered crystalline structure with different functionality. First, seeds of two different coordination polymers, A and B, are separately prepared such as by the solvothermal process. Time and heat may be applied to allow seeds of the coordination polymers A and B to grow. Typical crystallization temperatures range from ambient to 250° C., with reaction times from minutes to months. Most common are crystallizations that take a few hours to a few days at ambient to about 125° C. Examples of reactions times include from about 1 minute to about 5 months, or from about 2 hours to about 4 days. Suitable solvents include formamides, sulfoxides, nitriles, esters, amines, ethers, ketones, aromatics, aliphatics, water, and combinations thereof. Specific examples of solvents include, but are not limited to, ammonia, hexane, benzene, toluene, xylene, chlorobenzene, nitrobenzene, naphthalene, thipohene, pyridine, acetone, 1,2-dichloroethane, methylenechloride, tetrahydrofuran, ethanolamine, triethylamine, N.N-dimethyl formamide, N,N-diethyl formamide, methanol, ethanol, propanol, alcohols, dimethylsulfoxide, choloroform, bromoform, dibromomethane, iodoform, diiodomethane, halogenated organic solvents, N,N-dimethylacetamide, N,N-diethylacetamide, 1-methyl-2-pyrrolidinone, amide solvents, methylpyridine, dimethylpyridine, and mixtures thereof.

Then, a portion of the respective reaction solutions are exchanged. For example, a portion of the reaction solution containing seeds of coordination polymer A is added to the reaction solution for coordination polymer B; and a portion of the reaction solution containing seeds of coordination polymer B is added to the reaction solution for coordination polymer A. Of course, for purity, the seed-containing portions may be added to fresh reaction solutions instead of those used to generate the seeds. Time and heat may again be applied causing a new layer of coordination polymer to grow on top of the primary layer already present, see Example 3. The procedure may be stopped at this point with a coordination copolymer having two coordination polymers, one as a primary or core layer and the other as a layer over or surrounding the primary layer, such as a shell. Or, the procedure may continue with one or more iterations causing additional layers of coordination polymers to grow. The original two coordination polymers may be used to form alternating layers, or additional different coordination polymers may be used to create layers of different compositions. It is also within the scope of the invention to grow the first layer on a substrate with the second layer grown over the first layer and so on.

Through selecting different coordination polymers in the different layers, the coordination copolymer composition of matter may be engineered for a specific purpose. For example, a coordination polymer in the primary or core layer may contain large pore sizes, while a coordination polymer in the first layer over the primary layer may contain smaller pore sizes. In this way, the material may be used as a high capacity selective adsorbent. The smaller pore coordination polymer layer would operate to provide the selectivity, while the larger pore coordination polymer in the primary layer would operate to provide a high capacity. Tuning of the kinetics of guest uptake and release may be possible. Other properties of the coordination copolymer may be controlled in the same manner. Furthermore, multistage catalysts in a single material may be formed.

By selecting at least one coordination polymer that has a catalytic function, the coordination copolymer may be used as a catalyst to catalyze a reaction. For example, the coordination copolymer may be used in a process for converting at least one reactant by contacting a feed comprising at least one reactant with the coordination copolymer comprising at least a first coordination polymer and a second coordination polymer wherein the first and second coordination polymers are not identical and wherein at least one coordination polymer comprises a catalytic function, to give a converted product. In another example, the reaction may be a hydrocarbon conversion reaction where a feed comprising hydrocarbons is contacted with a coordination copolymer comprising at least a first coordination polymer and a second coordination polymer wherein the first and second coordination polymers are not identical and wherein at least one coordination polymer comprises a catalytic function, to give a converted product. Hydrocarbon conversion process include reactions such as cracking, hydrocracking, aromatic alkylation, isoparaffin alkylation, isomerization, polymerization, reforming, dewaxing, hydrogenation, dehydrogenation, transalkylation, dealkylation, hydration, dehydration, hydrotreating, hydrodenitrogenation, hydrodesulfurization, methanation, ring opening, and syngas shift. In another embodiment, the catalytic functionality may be added to the coordination copolymer after synthesis.

Examples 5-7 further demonstrate that a coordination polymer with a particular crystal habit can be successfully layered on crystals of a coordination polymer with a different crystal habit. In general this is a difficult task to carry out successfully because crystals tend to grow most effectively on seeds of the same morphology and crystal habit. For example, prisms grow best on prisms and cubes grow best on cubes. On the other hand, crystals can also be heterogeneously nucleated on nanoparticles present in reaction mixtures supersaturated with respect to the reagents necessary to the nucleation and growth of a given crystalline material. For example, ice crystals are heterogeneously nucleated and then continue to grow as snowflakes on nano dust particles in the atmosphere.

This process is enabled by preparing at least two types of crystals, but especially the crystal of the first, or core layer, in a small, or nano crystal size regime. In one embodiment, the nanocrystals can range from 10 to 100 nm, although crystals approaching 500 nm and even one micron in size can still be utilized as the core material. Often these nanocrystals are more irregular in habit and morphology than larger crystals of the same material. However, despite their nano size and often less-well pronounced crystal habit and morphology, the crystals can be easily identified by their characteristic powder XRD pattern. Likewise, when a second layer is grown on the surface of the first layer, the second material's characteristic XRD pattern will appear in the final product XRD pattern as a separate set of peaks.

A key benefit of this process is that the crystals of the second material can be grown on crystals of the first or core layer in the same reaction solution used to grow the first material. Such in situ or "one-pot" syntheses are of significant practical importance because of such issues as waste minimization and elimination of costly intermediate processing steps such as isolation and purification of the first material before subjecting the first material to the layering chemistry of the second layer. Nevertheless, in another embodiment of this invention, the crystals of the first layer are isolated and re-suspend in a supersaturated solution of the second material in order to grow the second material on the first material. This processing might be required where the solution chemistries or other processing conditions of the two materials are incompatible.

Another aspect of the "one-pot" Examples 5 through 7 is matching the chemistry of the material of the first or core layer with the chemistry of the second layer. This is important because, for example, the solvent for the first layer must be similar to, or the same as, the solvent for the second layer. This is because the reagents for the preparation of the second layer must be added to a suspension of the nanocrystals of the first layer. If the reagents for the preparation of the second material are insoluble in the solvent from the preparation of the first material, or if these reagents react with another soluble reagent left over in solution from the preparation of the first material, undesired by-products and/or precipitates may form. On the other hand, the chemistry of the preparation of the second material may be tailored in such a way as to react with, modify, and/or partially dissolve the crystals of the first material. The resultant second layer on a first material composite might then possess a highly desirable physical property such as enhanced porosity or crystal integrity.

In the examples, the selection of core and shell materials were based on the offset placement of XRD peaks for the two respective materials. The general design of these experiments involves reducing reactants for each product down to stoichiometric quantities, based on the molecular formula of the desired product. An equimolar amount of a base, such as triethylamine (TEA) was used per carboxylic acid function in order to facilitate coordination of linker to metal or metal clusters. The first or core material reaction is allowed to proceed for an appropriate period of time before the addition of pre-mixed reactants for the second material. Details are provided in Examples 5-7. Abbreviations as used in the examples include:

$H_3BTC$—1,3,5-benzenetricarboxylic acid
DMF—N,N-Dimethylformamide
EtOH—Ethyl alcohol
TEA—Triethylamine
$H_2BDC$—1,4-benzenedicarboxylic acid
Bipy—4,4'-bipyridyl
MOF formulas as used in the example include:
HKUST-1 $Cu_3BTC_2(H_2O)_3$
MOF-508 $ZnBDC(bipy)_{1/2} DMF(H_2O)_{1/2}$
IRMOF-1 $Zn_4O(BDC)_3$
MIL-53 $Al(OH)(BDC)(H_2BDC)_{0.7}$ As used in the examples below, an abbreviation of a coordination copolymer is as follows: a first MOF formula is recited, followed by the symbol @, followed by a second MOF formula. Multiple copolymers in a coordination copolymer are shown by reciting multiple MOF formulas, each separated from the others by the symbol @. For example, IRMOF-3@MOF-5 is used to describe the coordination copolymer containing both IRMOF-3 and MOF-5; and MOF-5@IRMOF-3@MOF-508 is used to describe the coordination copolymer containing all three of MOF-5, MOF-3, and MOF-508. Note that when the coordination copolymer has layers of MOFs, the order of the layers may be reflected in the abbreviation.

Figure 1A:
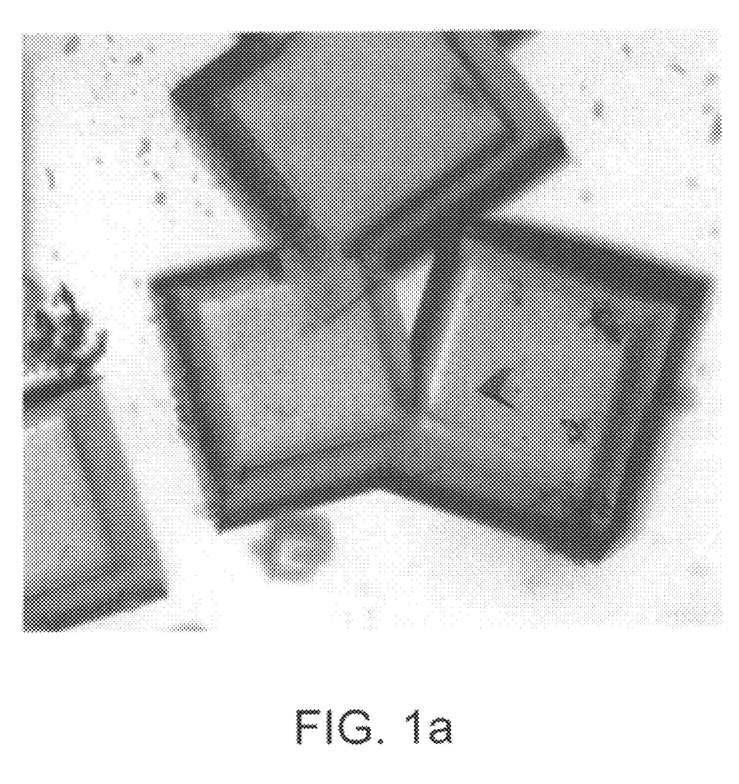
FIGS. 1a and 1b are microscope images of two-layer core-shell coordination copolymers of the present invention.
Figure 1B:
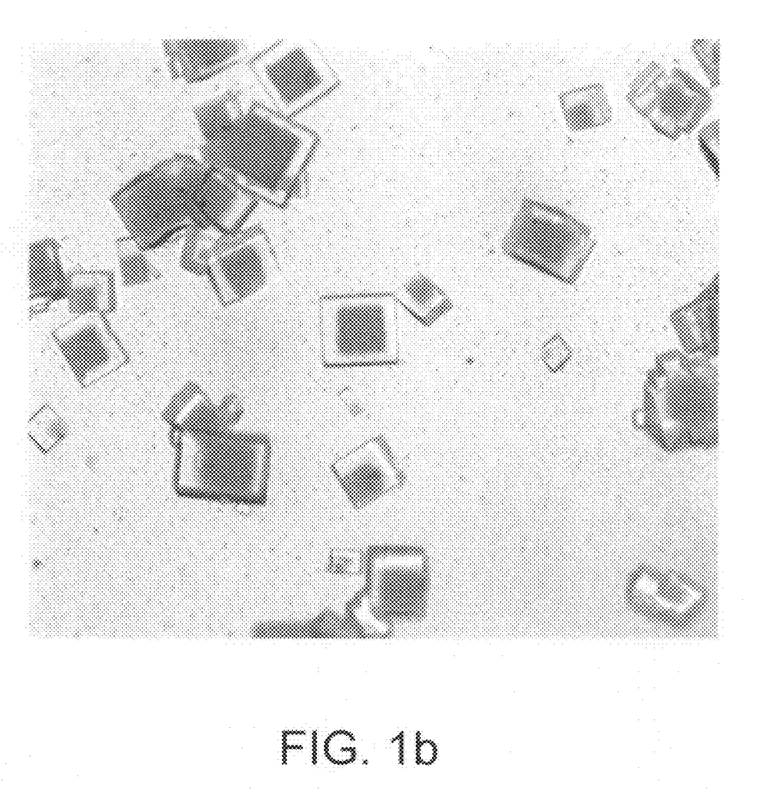

The coordination copolymer derived from the ditopic linker benzene-1,4-dicarboxylate (BDC) and 2-amino benzene-1,4-dicarboxylate (ABDC) serves to illustrate the invention. As background, it is noted that in the presence of zinc nitrate tetrahydrate and diethylforamide (DEF), pure benzene-1,4-dicarboxylic acid reacts to generate a coordination polymer, MOF-5, the crystal structure analysis of which shows it to be a simple cubic net in the Fm-3 m space group. Similarly, pure 2-amino benzene-1,4-dicarboxylic acid reacts to generate IRMOF-3 which has isostructure with MOF-5. As the first examples, seeds of MOF-5 and IRMOF-3 were separately prepared under the same solvothermal process as the synthesis of MOF-5. After 15 h, the respective reaction solutions were exchanged, i.e. seed crystals of MOF-5 were immersed in the unreacted solution of ABDC and $Zn(NO_3)_2$, and vice versa. Heating the solutions for another 15 h produced the coordination copolymers. The microscope image of the resultant products reveals core-shell cubes, see FIG. 1a and FIG. 1b, with color contrast corresponding to white (MOF-5) and orange (IRMOF-3). FIG. 1a shows IRMOF-3 as the shell layer and MOF-5 as the core layer, while FIG. 1b shows MOF-5 as the shell layer and IRMOF-3 as the core layer. The scale bar in FIGS. 1a and 1b is 200 µm. In both cases of MOF-5 and IRMOF-3 as seeds, core-shell-fashioned MOFs are successfully obtained. $^1$H NMR analysis after the decomposition with the core-shell MOFs showed that the molar composition of the block copolymer as BDC:ABDC=1:1, indicating the successful formation of MOF shells growing from the anchor points of carboxylate groups on the surface of seeded MOFs. The $N_2$ uptake of both core-shell MOFs are 820 cm$^3$/g for both IRMOF-3@MOF-5 and MOF-5@IRMOF-3, which are between that of MOF-5 (920 cm$^3$/g) and that of IRMOF-3 (750 cm$^3$/g).

Figure 2A:
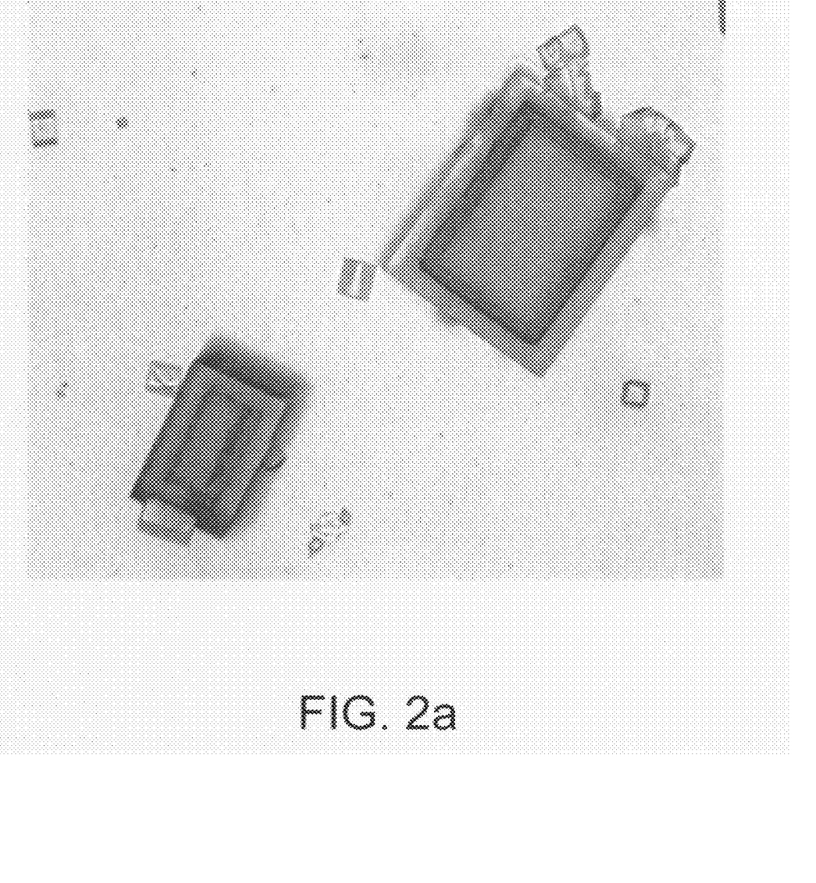
FIGS. 2a and 2b are microscope images of multilayered coordination copolymers of the present invention
Figure 2B:
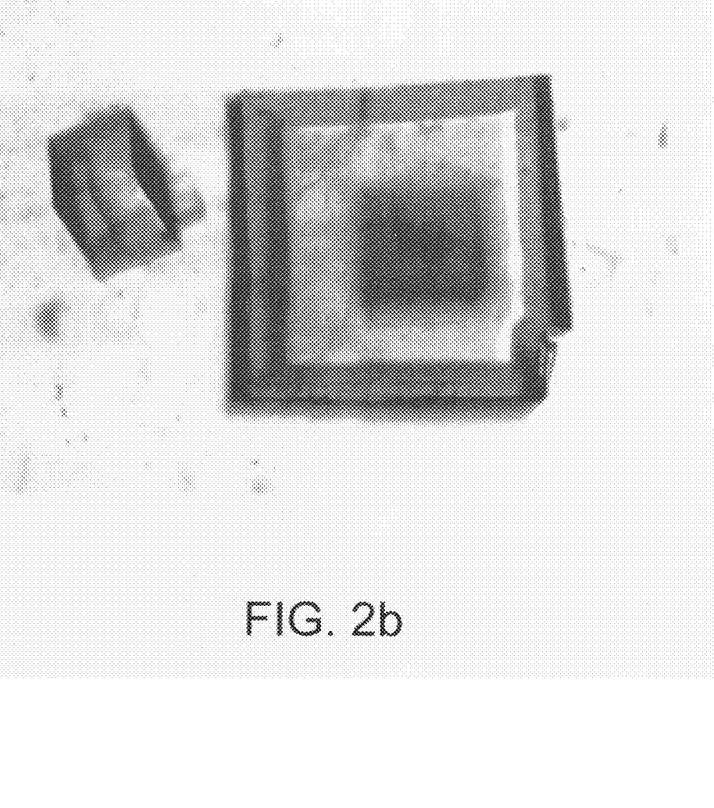

Applying the seed growth technique in presence of core-shell MOFs, the multilayered crystals can be also produced. Growth of new a layer from the core-shell seeds makes alternating of MOF-5 and IRMOF-3 layers. Two different multi-layered MOFs were successfully produced; MOF-5@IRMOF-3@MOF-5, as shown in FIG. 2a, and IRMOF-3@MOF-5@IRMOF-3, as shown in FIG. 2b. The scale bar in FIGS. 2a and 2b is 200 µm.

EXAMPLE 1

Preparation of Core-shell MOFs $H_2ABDC$ (48 mg, 0.26 mmol) and $H_2BDC$ (44 mg, 0.26 mmol) were charged to 20 mL of vials, separately. $Zn(NO_3)_2 \cdot 4H_2O$ (0.208 g, 0.795 mmol) and 10 mL of DEF were added to both vials. The mixtures were sonicated for 15 min and heated at 100° C. After 15 h, cubic-shaped crystals were formed in both solutions. Then both solutions were decanted and switched with each other. The mixtures were heated at 100° C. for another 15 h. The products were washed with DEF and then soaked in $CHCl_3$.

EXAMPLE 2

Preparation of Multilayered MOFs

The preparation of core-shell MOFs as seeds was carried out in the same way as described above in Example 1. After the formation of core-shell MOFs, the solution was decanted and the fresh mixture including $Zn(NO_3)_2 \cdot 4H_2O$ (0.208 g, 0.795 mmol) and $H_2ABDC$ (48 mg, 0.26 mmol) or $H_2BDC$ (44 mg, 0.26 mmol) in 10 mL of DEF was added. The mixtures were heated at 100° C. for another 15 h. The products were washed with DEF and then soaked in $CHCl_3$.

EXAMPLE 3

Post-modification of the Shell Part in the Core-shell MOFs

Wet state of core-shell MOF (IRMOF-3@MOF-5, 10 mg) and 10 mg of Cyclohexyl isocyante were mixed in 1 mL of Chloroform. The mixture was stirred by a shaking bath at room temperature for 3 days. After reaction, the products were washed with Chloroform.

EXAMPLE 4

Measurement of Diffusion of Nile Red into MOFs

Figure 3:
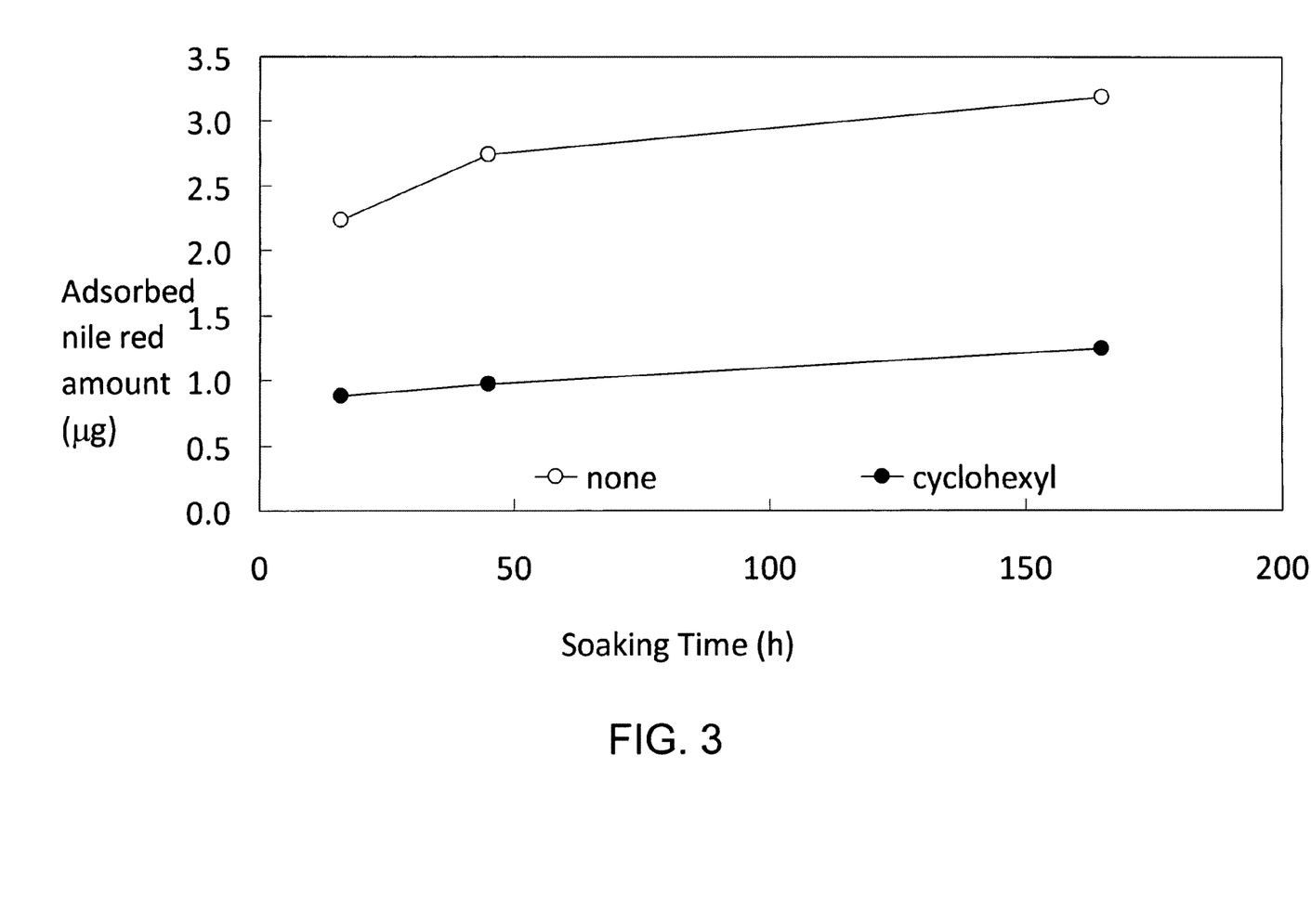
FIG. 3 is a plot of the amount of adsorbed nile red into (1) a coordination copolymer wherein the two coordination polymers of the coordination copolymer are IRMOF-3 and MOF-5 and (2) a coordination copolymer wherein the two coordination polymers of the coordination copolymer is a cyclohexyl modified IRMOF-3 and MOF-5, as a function of exposure time.

MOFs were soaked in 5 ppm of nile red solution in chloroform. In prescribed time, the absorbance of solutions was measured by a UV-vis spectrometer. Using the calibration curve, the nile red concentration in solutions was calculated. From the decrease of the nile red concentrations, the adsorbed amounts of the nile red into MOFs were measured. FIG. 3 is a plot of the amount of adsorbed nile red into (1) a coordination copolymer wherein the two coordination polymers of the coordination copolymer are IRMOF-3 and MOF-5 and (2) a coordination copolymer wherein the two coordination polymers of the coordination copolymer is a cyclohexyl modified IRMOF-3 and MOF-5, as a function of exposure time.

EXAMPLE 5

NanoMOF-508 on NanoHKUST-1

A suspension of nanoHKUST-1 was prepared by adding $H_3BTC$ (0.5 g, 2.38 mmol), DMF (8.3 mL), EtOH (8.3 mL), water (8.3 mL), and copper (II) nitrate (0.83 g, 3.57 mmol) to a glass jar with magnetic stirring at room temperature. TEA (1 mL, 7.14 mmol) was slowly added, the jar sealed, and the cloudy blue suspension stirred at room temperature for 3.5 hours. Meanwhile, a clear, colorless solution of $H_2BDC$ (0.38 g, 2.37 mmol), DMF (50 mL), EtOH (50 mL), bipy (0.19 g, 1.18 mmol), and zinc (II) nitrate (0.70 g, 2.37 mmol) was prepared in a glass beaker with magnetic stirring at room temperature. This clear, colorless solution was slowly added to the nanoHKUST-1 suspension above, the jar sealed, and the mixture stirred. After 3 hours the suspension pH was 2-3. A TEA/DMF/EtOH (0.6, 41.7, 41.7 mL) solution was then slowly added dropwise to the mixture, which was finally sealed and allowed to stir overnight. The turquoise solid was separated from the clear, colorless liquid (p~5) by filtration through 0.45 µm filter paper, and then dried in a 60° C. oven under nitrogen overnight. Elemental analysis via inductively coupled plasma (ICP) on the filtrate solution revealed that <0.0001 mass % of Zn and Cu remained in solution after the reaction. Meanwhile, the XRD powder pattern for the solid material showed peaks for both MOF-508 and HKUST-1, and ICP elemental analysis on the solid product revealed the presence of both metals, Cu and Zn.

EXAMPLE 6

NanoMOF-508 on NanoIRMOF-1

A suspension of nanoIRMOF-1 was prepared by adding $H_2BDC$ (0.85 g, 5 mmol), DMF (100 mL), and zinc (II) nitrate (3.0 g, 10 mmol) to a glass jar with magnetic stirring at room temperature. TEA (1.4 mL, 10 mmol) was slowly added, the jar sealed, and the cloudy white suspension stirred at room temperature for 3.5 hours. Meanwhile, a suspension of $H_2BDC$ (0.38 g, 2.37 mmol), EtOH (50 mL), bipy (0.19 g, 1.18 mmol), and zinc (II) nitrate (0.70 g, 2.37 mmol) was prepared in a glass beaker with magnetic stirring at room temperature. This milky suspension was slowly added to the nanoIRMOF-1 suspension above, the jar sealed, and the mixture stirred. After 3 hours the suspension pH was 3-3.5. A TEA/EtOH (0.7, 50 mL) solution was slowly added dropwise to the mixture, which was finally sealed and allowed to stir overnight. The white solid was separated from the clear, colorless liquid (pH approximately 4) by filtration through 0.45 µm filter paper, and then dried in a 60° C. oven under nitrogen overnight. Elemental analysis on the filtrate solution revealed about 0.16 mass % of Zn remained in solution after the reaction. Meanwhile, the XRD powder pattern for the solid material showed peaks for both MOF-508 and IRMOF-1, and elemental analysis on the solid product revealed the presence of Zn.

EXAMPLE 7

NanoMIL-53 on NanoHKUST-1

A suspension of nanoHKUST-1 was prepared by adding $H_3BTC$ (0.5 g, 2.38 mmol), DMF (8.3 mL), EtOH (8.3 mL), $H_2O$ (8.3 mL), and copper (II) nitrate (0.83 g, 3.57 mmol) to a glass jar with magnetic stirring at room temperature. TEA (1 mL, 7.14 mmol) was slowly added, the jar sealed, and the cloudy blue suspension stirred at room temperature for 3.5 hours. Meanwhile, a suspension of $H_2BDC$ (0.58 g, 3.5 mmol), DMF (10 mL), EtOH (10 mL), $H_2O$ (10 mL) and aluminum (III) nitrate (2.6 g, 6.9 mmol) was prepared in a glass beaker with magnetic stirring at room temperature. The cloudy white suspension was slowly added to the nanoHKUST-1 suspension above, the jar sealed, and the mixture stirred. After 3 hours the suspension pH was 1.5-2.5. A TEA/DMF/EtOH/H2O (0.96, 7.7, 7.7, 8.7 mL) solution was slowly added drop-wise to the mixture which was finally sealed and stirred overnight. The blue suspension was centrifuged at about 15,000 relative centrifugal force (rcf) for 1 hour, the mother liquor at pH 2-3 was decanted, and the solids were dried in a 50° C. oven under nitrogen overnight. The XRD powder pattern for the solid material showed peaks for both MIL-53 and HKUST-1, and elemental analysis on the mother liquor revealed 0.094 mass % Cu and 0.11 mass % Al in solution.

The invention claimed is:
1. A process for separating a first component from a second component of a mixture comprising contacting the mixture with a coordination copolymer comprising at least a first region of a first coordination polymer having a first x-ray diffraction pattern and second region of a second coordination polymer having a second x-ray diffraction pattern wherein the first and second coordination polymers are not identical and wherein the x-ray diffraction pattern of the coordination copolymer comprises both the first x-ray diffraction pattern and the second x-ray diffraction pattern.

2. The process of claim 1 wherein the first coordination polymer and the second coordination polymer are present in a first and second layered configuration.

3. The process of claim 2 wherein the coordination copolymer further comprises at least a third coordination polymer layered on the second layer.

4. The process of claim 3 wherein the third coordination polymer is identical in composition to the first coordination polymer.

5. The process of claim 3 wherein the composition of the third coordination polymer is different from that of the first coordination polymer and the second coordination polymer.

6. The process of claim 3 wherein the third coordination polymer is identical in structure to the first coordination polymer.

7. The process of claim 3 wherein the structure of the third coordination polymer is different from that of the first coordination polymer and the second coordination polymer.

8. The process of claim 2 wherein the first and second layered configuration form a core and shell configuration.

9. The process of claim 8 further comprising at least a third coordination polymer layered on the shell.

10. The process of claim 8 wherein the first coordination polymer located in the core has a greater average pore size than the second coordination polymer located in the shell.

11. The process of claim 1 wherein the first component permeates the first coordination polymer while the second component does not permeate the first coordination polymer.

12. The process of claim 1 wherein the first component permeates the second coordination polymer while the second component does not permeate the second coordination polymer.

13. The process of claim 1 wherein the first component is retained by the coordination copolymer while the second component is not retained by the coordination copolymer.

14. The process of claim 13 further comprising desorbing the first component from the coordination copolymer.

15. The process of claim 14 wherein the desorbing involves contacting the coordination copolymer with a desorbent.

* * * * *